(12) United States Patent  
Enomoto

(10) Patent No.: US 8,710,992 B2  
(45) Date of Patent: Apr. 29, 2014

(54) BIOLOGICAL INFORMATION MONITORING SYSTEM

(75) Inventor: Yoshinori Enomoto, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 118 days.

(21) Appl. No.: 13/528,452

(22) Filed: Jun. 20, 2012

(65) Prior Publication Data

US 2013/0002431 A1 Jan. 3, 2013

(30) Foreign Application Priority Data

Jun. 30, 2011 (JP) .................................. 2011-145613

(51) Int. Cl.
*G08B 23/00* (2006.01)

(52) U.S. Cl.
USPC .......................... 340/573.1; 340/5.1; 600/301

(58) Field of Classification Search
USPC ............... 340/573.1, 4.3, 5.1, 9.1, 9.11, 9.15; 600/300, 301
See application file for complete search history.

(56) References Cited

U.S. PATENT DOCUMENTS

| | | | |
|---|---|---|---|
| 7,595,723 B2 * | 9/2009 | Heitzmann et al. | 340/539.12 |
| 2006/0183972 A1 | 8/2006 | Tashiro et al. | |
| 2009/0171169 A1 | 7/2009 | Nagata et al. | |
| 2011/0090056 A1 | 4/2011 | Kawasaki et al. | |

FOREIGN PATENT DOCUMENTS

| | | |
|---|---|---|
| EP | 2428158 A2 | 9/2011 |
| JP | 2005-229426 A | 8/2005 |
| JP | 2010-11281 A | 1/2010 |

OTHER PUBLICATIONS

European Search Report dated Oct. 11, 2012 issued by the European Patent Office in counterpart European Application No. 12173347.1.

* cited by examiner

*Primary Examiner* — Toan N Pham

(74) *Attorney, Agent, or Firm* — Sughrue Mion, PLLC

(57) ABSTRACT

A biological information monitoring system includes: a transmitter to which first channel information is allocated, the transmitter collecting biological information from a living body and outputting the biological information; a first receiver in which the first channel information is set, the first receiver receiving the biological information from the transmitter to which the first channel information is allocated, the first receiver outputting the biological information; a monitoring apparatus receiving the biological information from the first receiver and displaying the received biological information; a setting unit setting the first channel information in the first receiver; a second receiver in which second channel information is set; and a detector determining whether the first channel information is identical with the second channel information.

6 Claims, 6 Drawing Sheets

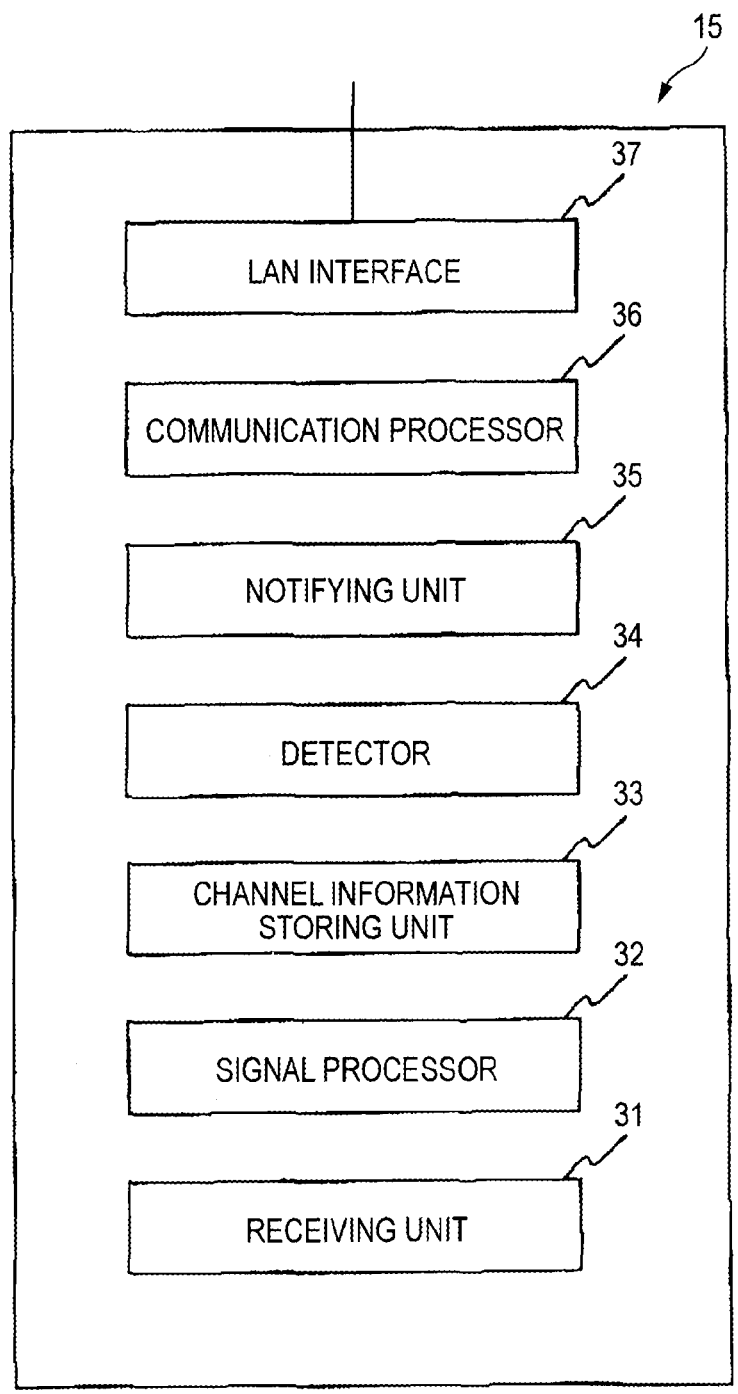

FIG. 3

| STORAGE AREA FOR OWN APPARATUS | | STORAGE AREAS FOR OTHER APPARATUSES | | | |
|---|---|---|---|---|---|
| BED ID/CHANNEL INFORMATION<br>IP ADDRESS OF CENTRAL MONITOR | BED ID/CHANNEL INFORMATION<br>IP ADDRESS OF CENTRAL MONITOR | BED ID/CHANNEL INFORMATION<br>IP ADDRESS OF CENTRAL MONITOR | BED ID/CHANNEL INFORMATION<br>IP ADDRESS OF CENTRAL MONITOR | | BED ID/CHANNEL INFORMATION<br>IP ADDRESS OF CENTRAL MONITOR |
| BED 1/1001<br>IP ADDRESS OF CENTRAL MONITOR | BED 11/2001<br>IP ADDRESS OF CENTRAL MONITOR | BED 21/3001<br>IP ADDRESS OF CENTRAL MONITOR | | | BED 81/6001<br>IP ADDRESS OF CENTRAL MONITOR |
| BED 2/1002<br>IP ADDRESS OF CENTRAL MONITOR | ⋮ | ⋮ | ⋮ | | ⋮ |
| ⋮ | ⋮ | ⋮ | ⋮ | | ⋮ |
| ⋮ | ⋮ | ⋮ | ⋮ | | ⋮ |
| ⋮ | ⋮ | ⋮ | ⋮ | | ⋮ |
| BED 8/1008<br>IP ADDRESS OF CENTRAL MONITOR | BED 18/2008<br>IP ADDRESS OF CENTRAL MONITOR | BED 28/3008<br>IP ADDRESS OF CENTRAL MONITOR | | | BED 88/6008<br>IP ADDRESS OF CENTRAL MONITOR |
| IP ADDRESS OF OWN APPARATUS | | | | | |

FIG. 5

| AREA NO. | PATIENT NAME PATIENT ID | IP ADDRESS OF RECEIVING DESTINATION BED ID/CHANNEL INFORMATION | AREA NO. | PATIENT NAME PATIENT ID | IP ADDRESS OF RECEIVING DESTINATION BED ID/CHANNEL INFORMATION |
|---|---|---|---|---|---|
| 1 | | | 9 | | |
| 2 | | | 10 | | |
| ... | | | ... | | |
| 8 | | | 16 | | |

BIOLOGICAL INFORMATION MONITORING SYSTEM

BACKGROUND OF THE INVENTION

The present invention relates to a biological information monitoring system including a plurality of transmitters to which individual channel information is allocated, which collect biological information from respective living bodies, and which transmit the biological information.

A biological information monitoring system includes a plurality of receivers which, when channel information is set, receive biological information that is collected by a transmitter to which the set channel information is allocated, and which transmits the biological information via a network. The system is configured so that, depending on the settings of the channel information for the receivers, a central monitor collects the biological information from a patient.

When the channel information of a transmitter which is placed for a patient who is not a monitor object is set in the receivers, therefore, there is a possibility that the biological information of the patient who is to be monitored may not be monitored, or that misidentification of patients may occur. As a function of coping with the above situation, it is checked, in the central monitor, only whether the correspondence relationship between the patient and the channel information is adequate or not. This countermeasure is insufficient.

By contrast, JP-A-2010-11281 describes a system in which, in order to obtain a desired image, a plurality of images obtained from a plurality of video receivers are displayed like thumbnail images in an arranged manner on one screen, and the desired image can be selected on the screen. In the system, a desired image or biological information can be obtained without causing an input error. However, it is difficult for the system to cope with duplicate settings of channels.

In order to avoid an erroneous setting of a user ID in a telemeter system, JP-A-2005-229426 describes apparatuses in which, in two radio apparatuses which communicate with each other, default user IDs are set to be identical with the radio identification numbers specific to the respective radio apparatuses. According to the configuration, an erroneous setting of a user ID can be avoided in the initial stage. In a biological information monitoring system in which patients are changed to alter monitor objects with an elapse of time and date, however, an erroneous setting cannot be avoided because the setting of channel information must be altered at each change.

SUMMARY

This invention provides a biological information monitoring system in which it is possible to detect that duplicate settings of channel information occur, and therefore a situation where biological information of a desired patient cannot be monitored, or that where misidentification of patients is caused can be adequately prevented from occurring.

One aspect of the invention provides a biological information monitoring system comprising: a transmitter to which first channel information is allocated, the transmitter operable to collect biological information from a living body and operable to output the biological information; a first receiver in which the first channel information is set, the first receiver operable to receive the biological information from the transmitter to which the first channel information is allocated, the first receiver operable to output the biological information; a monitoring apparatus operable to receive the biological information from the first receiver and operable to display the received biological information; a setting unit operable to set the first channel information in the first receiver; a second receiver in which second channel information is set; and a detector operable to determine whether the first channel information set in the first receiver is identical with the second channel information set in the second receiver.

The biological information monitoring system may further include a notifying unit, when the detector determines that the first channel information set in the first receiver is identical with the second channel information set in the second receiver, operable to perform notification of duplicate settings.

The biological information monitoring system may further include an alarm outputting unit, in response to the notification performed by the notifying unit, operable to output an alarm. The setting unit may be disposed in the monitoring apparatus, the detector and the notifying unit may be disposed in the first receiver, and the alarm outputting unit may be disposed in the monitoring apparatus.

The biological information monitoring system may further include an alarm outputting unit, in response to the notification performed by the notifying unit, operable to output an alarm. The setting unit may be disposed in the monitoring apparatus, the detector and the notifying unit may be disposed in a computer connected to a network, and the alarm outputting unit may be disposed in the monitoring apparatus.

The biological information monitoring system may further include an alarm outputting unit, in response to the notification performed by the notifying unit, operable to output an alarm. The setting unit, the detector, the notifying unit and the alarm outputting unit may be disposed in the monitoring apparatus.

The biological information monitoring system may further include a forcible setting unit, when the detector determines that the first channel information set in the first receiver is identical with the second channel information set in the second receiver, operable to set the determination to be valid or invalid.

BRIEF DESCRIPTION OF THE DRAWINGS

FIG. 2 is a block diagram illustrating the configuration of an embodiment of a receiver in the biological information monitoring system of the invention.

FIG. 3 is a view illustrating an example of information stored in a storing unit disposed in the embodiment of the receiver in the biological information monitoring system of the invention.

FIG. 5 is a view illustrating an example of information stored in a table disposed in an embodiment of the central monitor in the biological information monitoring system of the invention.

DETAILED DESCRIPTION OF EMBODIMENTS

Figure 1:
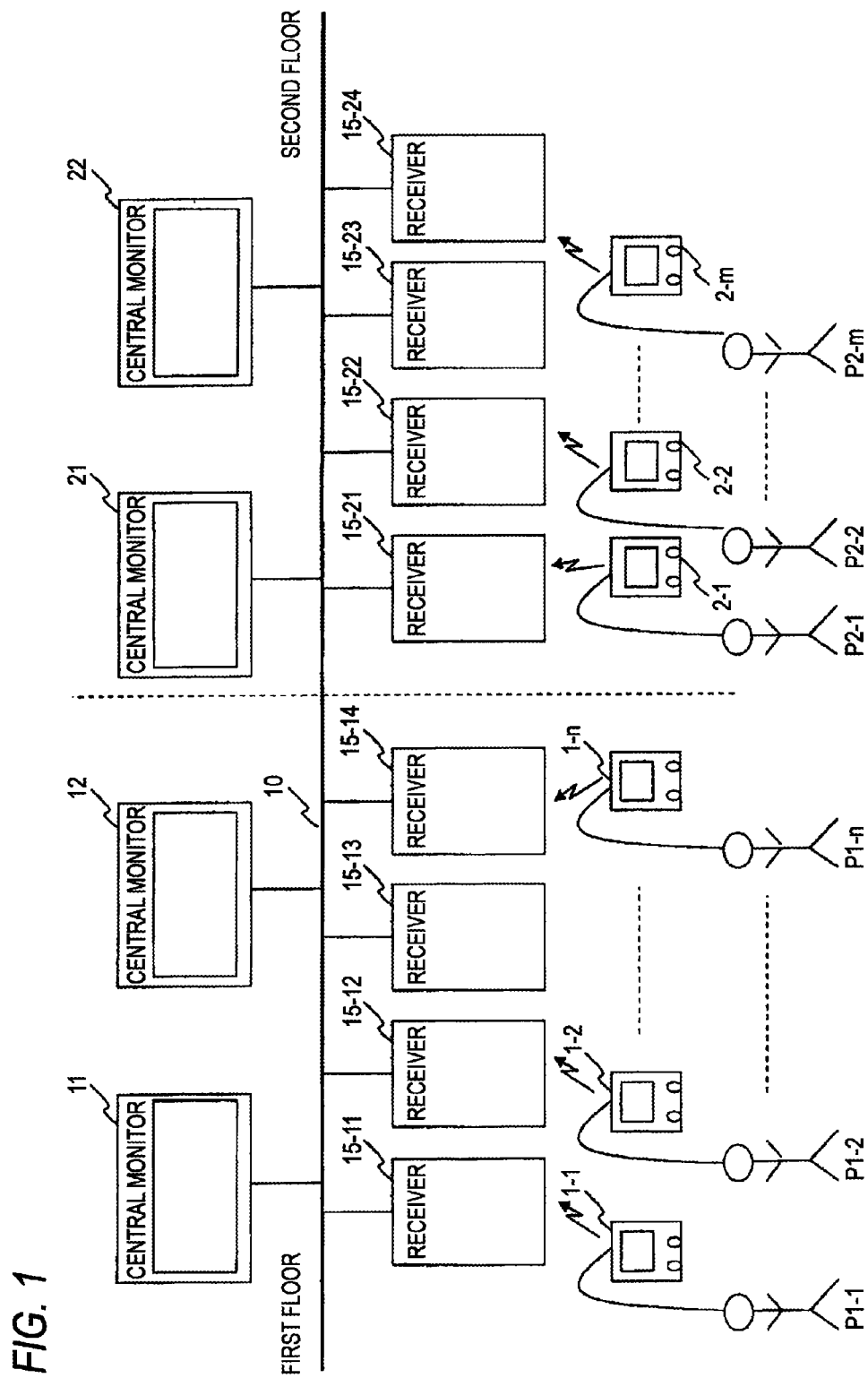
FIG. 1 is a block diagram illustrating the configuration of an embodiment of the biological information monitoring system of the invention.

Hereinafter, an embodiment of the biological information monitoring system of the invention will be described with reference to the accompanying drawings. In the figures, the identical components are denoted by the same reference numerals, and duplicated description is omitted. FIG. 1 is a diagram of an embodiment of the biological information monitoring system of the invention. The system has two sets of two central monitors 11, 12 and 21, 22 placed on, for example, the first and second floors, respectively. The central monitors 11, 12, 21, 22 are connected to a LAN 10 which is a network that performs communication via IP protocol.

For example, four receivers 15-11 to 15-14 on the first floor, and four receivers 15-21 to 15-24 on the second floor are connected to the LAN 10. Moreover, transmitters 1-1 to 1-n are attached to patients P1-1 to P1-n, and transmitters 2-1 to 2-m are attached to patients P2-1 to P2-m, respectively.

The transmitters 1-1 to 1-n, 2-1 to 2-m are allocated with respective individual channel information, collect biological information from respective patients, and transmit the biological information. Electrodes or the like which detect biological information are adhered to the patients P1-1 to P1-n, P2-1 to P2-m, and connected to the transmitters 1-1 to 1-n, 2-1 to 2-m through lead wires, respectively. The transmitters can collect various kinds of biological information such as electrocardiogram data, respiration data, the blood pressure, the SpO2, and CO2.

Each of the above-described receivers 15-11 to 15-14, 15-21 to 15-24 is configured to, receive setting of channel information, receive biological information that is collected by a transmitter to which the set channel information is allocated, and output the biological information via the LAN 10 that is a network. The central monitors 11, 12, 21, 22 receive biological information output from the receivers 15-11 to 15-14, 15-21 to 15-24, and output the waveform and value of the received biological information.

The receivers 15-11 to 15-14, 15-21 to 15-24 have identical or functionally identical or similar components, and have the configuration of a receiver 15 shown in FIG. 2. Each of the receivers 15 includes a receiving unit 31 which receives a signal sent from a transmitter. A signal received by the receiving unit 31 is fetched into a signal processor 32, and undergoes necessary processes. The necessary processes basically include digitization for transmission to the LAN 10, and the like. Depending on the setting on the side of the central monitor, the processes may include a process of setting an alarm, or a signal process such as the arrhythmia analysis.

The receiver 15 further includes a channel information storing unit 33, a detector 34, a notifying unit 35, a communication processor 36, and a LAN interface 37. In the channel information storing unit 33, channel information indicating the maximum number (in the embodiment, eight) of transmitters from which the receiver 15 can collect channel information is stored in correspondence with, for example, a bed ID. As shown in FIG. 3, the channel information storing unit 33 stores channel information of transmitters which collect biological information from patients to whom beds having bed IDs of Bed 1 to Bed 8 for the own apparatus are allocated, and the IP address of a central monitor in which the channel information is set. The IP address of the own apparatus is stored in the lowest area.

The detector 34 collects channel information which is set in the other receivers, and determines whether the channel information set in the channel information storing unit 33 included in the receiver (own receiver) 15 is identical with the collected channel information set in the other receivers. In other words, the detector 34 detects settings of the same channel information (duplicate settings). For example, the collection of channel information may be performed after every elapse of a predetermined time period. The collected channel information of the other receivers is stored in a storage area for other apparatuses in the channel information storing unit 33 shown in FIG. 3, together with the bed IDs. When the detector 34 detects settings of the same channel information, the notifying unit 35 notifies of the duplicate settings by using the IP address of the central monitor which sets the channel information, as a destination address. The IP address is stored in the channel information storing unit 33. In response to the notification from the notifying unit 35, an alarm generator 43 generates an audible alarm, and a visible alarm is displayed in a corresponding area of a screen of a display 42.

The LAN interface 37 performs communication via IP protocol through the LAN 10. The communication processor 36 performs processes such as formatting of data to be transmitted, and decomposition of received data.

Figure 4:
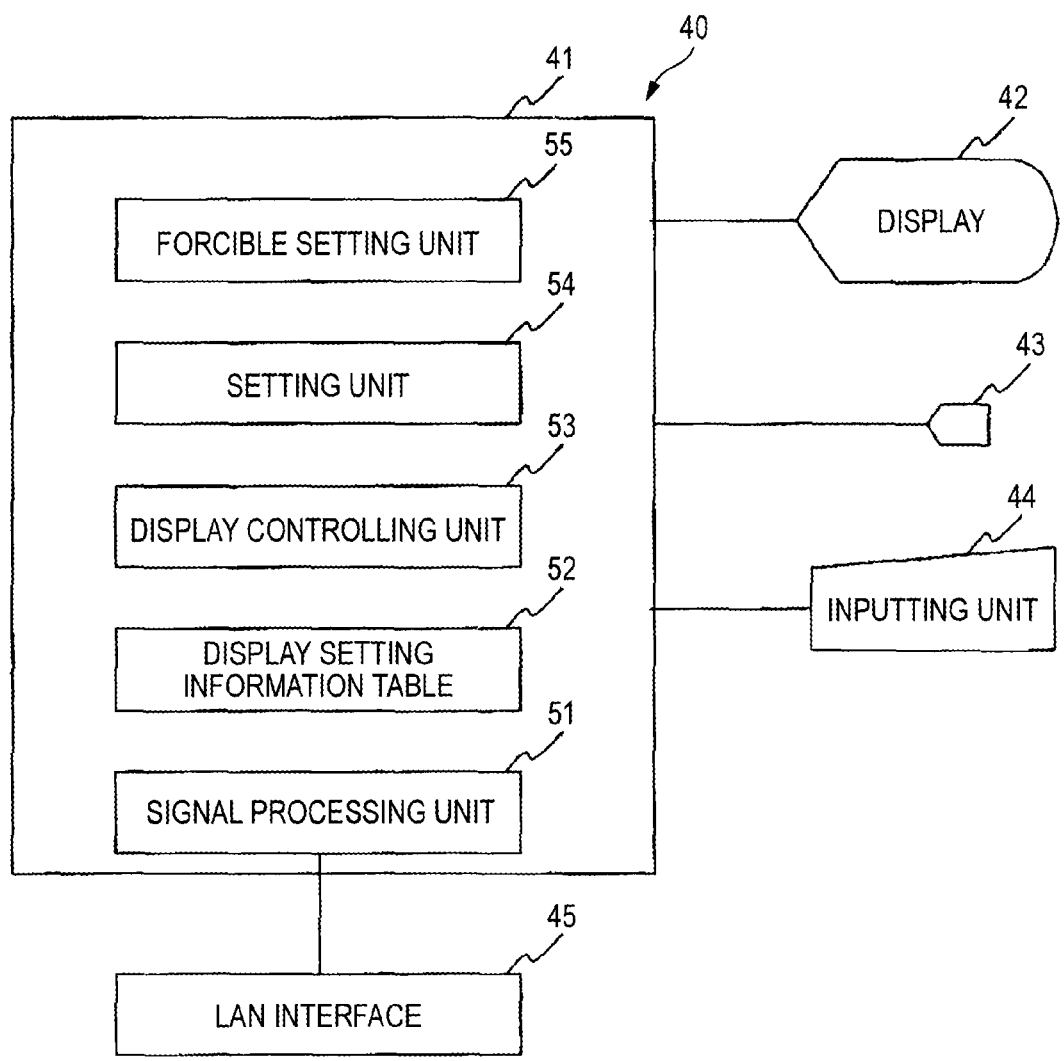
FIG. 4 is a block diagram illustrating the configuration of an embodiment of a central monitor in the biological information monitoring system of the invention.

The central monitors 11, 12, 21, 22 have identical or functionally identical or similar components, and have the configuration of a central monitor 40 shown in FIG. 4. Namely, the central monitors have the configuration where the display 42, the alarm generator 43, an inputting unit 44, and a LAN interface 45 are connected to a main unit 41 which is configured by a computer or the like. The display 42 is configured by a displaying apparatus such as an LED or an LCD, and can display the waveforms and values of various kinds of biological information. The alarm generator 43 can include a speaker or the like which generates the audible alarm.

The inputting unit 44 can include a keyboard and a pointing device such as a mouse, so that various data and commands can be input through the inputting unit. The LAN interface 45 performs communication via IP protocol through the LAN 10.

The main unit 41 includes a signal processing unit 51, a display setting information table 52, a display controlling unit 53, a setting unit 54, and a forcible setting unit 55. The signal processing unit 51 performs processes such as formatting of data to be transmitted, and decomposition of received data.

The display setting information table 52 is a table in which, for example, various kinds of information that is to be displayed on the display 42, and that is related to biological information for 16 areas are set. As shown in FIG. 5, for example, the table is configured so that the name of a patient, a patient ID, the IP address of a receiver which collects biological information, and Bed ID/channel information are stored for each area number.

Figure 6A:
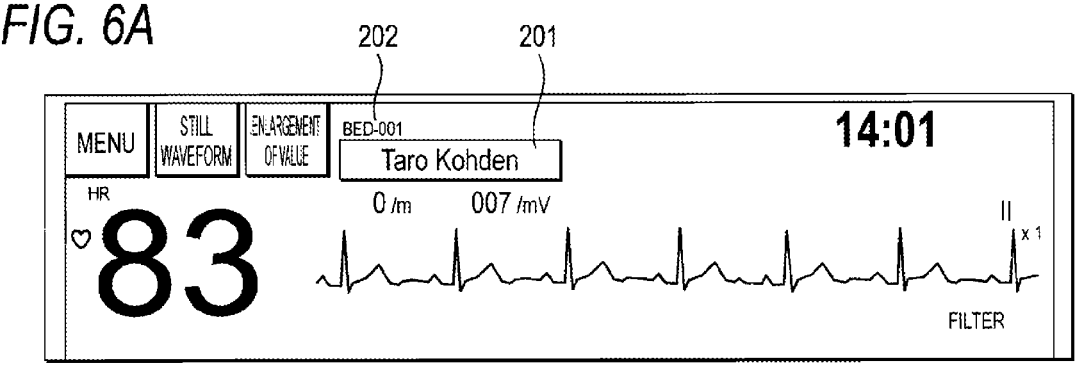
FIGS. 6A and 6B are views illustrating examples of information displayed on a display of the central monitor in the biological information monitoring system of the invention.
Figure 6B:
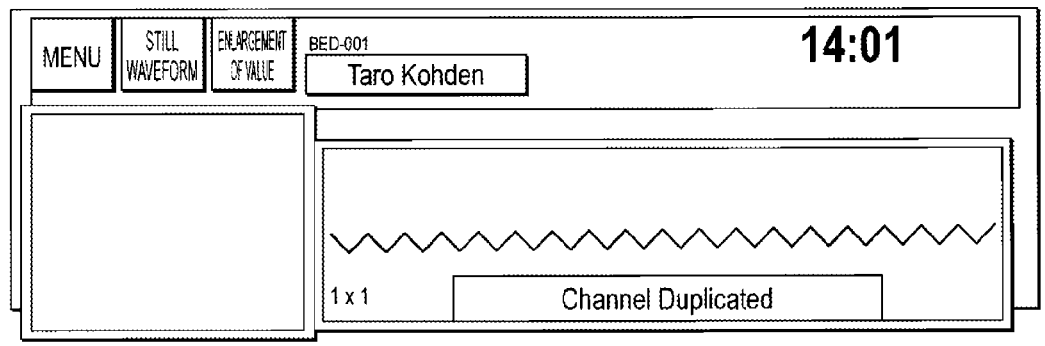

The display controlling unit 53 causes biological information which is sent from a receiver of an IP address stored in the display setting information table 52, which arrives through the LAN interface 45, and which is separated by the signal processing unit 51, to be displayed in a corresponding area of the screen of the display 42, based on the stored contents of the display setting information table 52. FIG. 6A illustrates a display example of biological information and the like which are displayed in a certain area. The patient name 201, the bed ID 202, and the like are displayed together with the waveform and value of the biological information. It is determined whether the information output from the receiver indicates notification information or biological information. In the case of outputting biological information, the waveform and the value are displayed as shown in FIG. 6A. In the case of outputting notification information, a visible alarm indicative of duplicated channel information is displayed in a corresponding area of the screen of the display 42 as shown in FIG. 6B.

The setting unit 54 sets, in a receiver, the channel information of a transmitter which collects biological information to be received by a central monitor that is a monitoring apparatus. The IP address of a receiver which collects biological information, and Bed ID/channel information are registered in an area of the display setting information table 52, whereby a setting into the receiver is performed.

In the case where settings of the same channel information are detected by the detector 34 of a receiver, the forcible setting unit 55 sets the settings valid in response to an operation through the inputting unit 44. In the case where settings of the same channel information are detected by the detector 34, when the settings are made invalid by the forcible setting unit 55, the setting unit 54 does not perform a setting of the latter channel information (the channel information which is to be set at this time), and, when the settings are made valid by the forcible setting unit 55, performs a setting of the latter channel information. In the case where settings of the same channel information are detected, namely, the storing of the channel information into the corresponding area of the display setting information table 52 is suspended.

In the above-described configuration, the forcible setting unit 55 is disposed in each of the central monitors. Alternatively, the forcible setting unit 55 may be disposed only in required central monitors. The monitoring and notification of overlapping of channel information are performed in the receiver 15. The invention is not limited to this. For example, each central monitor may include the channel information storing unit 33, the detector 34, and the notifying unit 35 to have the monitoring and notification functions. Alternatively, a computer such as a personal computer may include the channel information storing unit 33, the detector 34, and the notifying unit 35, and connected to the LAN 10. The computer may perform the monitoring and notification of overlapping of channel information.

In any one of the biological information monitoring systems having the above-described configurations, channel information which is set in the receiver is collected, settings of the same channel information is detected, and, when settings of the same channel information are detected, the duplicate settings are notified. In the case where duplicate settings of channel information occur, therefore, the system can detect and notify of the occurrence.

According to an aspect of the invention, the biological information monitoring system collects channel information which is set in the receiver, detects settings of the same channel information, and, when settings of the same channel information are detected, notifies of the duplicate settings. In the case where duplicate settings of channel information occur, therefore, the system can detect and notify of the occurrence.

According to an aspect of the invention, the biological information monitoring system sets the detection to be valid or invalid, when settings of the same channel information are detected. Therefore, a plurality of monitoring apparatuses can perform monitoring while obtaining biological information which is collected by transmitters of the same channel, and the system can be conveniently operated.

What is claimed is:

1. A biological information monitoring system comprising:
   a transmitter to which first channel information is allocated, the transmitter operable to collect biological information from a living body and operable to output the biological information;
   a first receiver in which the first channel information is set, the first receiver operable to receive the biological information from the transmitter to which the first channel information is allocated, the first receiver operable to output the biological information;
   a monitoring apparatus operable to receive the biological information from the first receiver and operable to display the received biological information;
   a setting unit operable to set the first channel information in the first receiver;
   a second receiver in which second channel information is set; and
   a detector operable to determine whether the first channel information set in the first receiver is identical with the second channel information set in the second receiver.

2. The biological information monitoring system according to claim 1, further comprising a notifying unit, when the detector determines that the first channel information set in the first receiver is identical with the second channel information set in the second receiver, operable to perform notification of duplicate settings.

3. The biological information monitoring system according to claim 2, further comprising an alarm outputting unit, in response to the notification performed by the notifying unit, operable to output an alarm, wherein
   the setting unit is disposed in the monitoring apparatus,
   the detector and the notifying unit are disposed in the first receiver, and
   the alarm outputting unit is disposed in the monitoring apparatus.

4. The biological information monitoring system according to claim 2, further comprising an alarm outputting unit, in response to the notification performed by the notifying unit, operable to output an alarm, wherein
   the setting unit is disposed in the monitoring apparatus,
   the detecting unit and the notifying unit are disposed in a computer connected to a network, and
   the alarm outputting unit is disposed in the monitoring apparatus.

5. The biological information monitoring system according to claim 2, further comprising an alarm outputting unit, in response to the notification performed by the notifying unit, operable to output an alarm, wherein
   the setting unit, the detector, the notifying unit and the alarm outputting unit are disposed in the monitoring apparatus.

6. The biological information monitoring system according to claim 1, further comprising a forcible setting unit, when the detector determines that the first channel information set in the first receiver is identical with the second channel information set in the second receiver, operable to set the determination to be valid or invalid.

* * * * *